(12) United States Patent
Yamamoto et al.

(10) Patent No.: US 9,849,272 B2
(45) Date of Patent: Dec. 26, 2017

(54) APPLICATOR

(71) Applicant: HISAMITSU PHARMACEUTICAL CO., INC., Tosu-shi, Saga (JP)

(72) Inventors: Naoki Yamamoto, Tsukuba (JP); Makoto Ogura, Tsukuba (JP)

(73) Assignee: HISAMITSU PHARMACEUTICAL CO., INC., Tosu-Shi, Saga (JP)

( * ) Notice: Subject to any disclaimer, the term of this patent is extended or adjusted under 35 U.S.C. 154(b) by 0 days.

(21) Appl. No.: 14/899,146

(22) PCT Filed: Jun. 17, 2014

(86) PCT No.: PCT/JP2014/066070
§ 371 (c)(1),
(2) Date: Dec. 17, 2015

(87) PCT Pub. No.: WO2014/203911
PCT Pub. Date: Dec. 24, 2014

(65) Prior Publication Data
US 2016/0136405 A1    May 19, 2016

(30) Foreign Application Priority Data

Jun. 18, 2013 (JP) ................................. 2013-127492
Jun. 19, 2013 (JP) ................................. 2013-128624

(51) Int. Cl.
*A61M 5/00* (2006.01)
*A61M 37/00* (2006.01)
(Continued)

(52) U.S. Cl.
CPC ...... *A61M 37/0015* (2013.01); *A61M 25/002* (2013.01); *A61M 35/00* (2013.01);
(Continued)

(58) Field of Classification Search
CPC ...... A61M 37/0015; A61M 2037/0023; A61M 2037/0046; A61M 2037/0061
(Continued)

(56) References Cited

U.S. PATENT DOCUMENTS 6,589,202 B1 * 7/2003 Powell ............... A61B 10/0045
604/27
2002/0091357 A1    7/2002 Trautman et al.
(Continued)

FOREIGN PATENT DOCUMENTS

AU    2012200649 A1    2/2012
EP       1360935 A1    11/2003
(Continued)

OTHER PUBLICATIONS

IPRP issued in international application No. PCT/JP2014/066070 dated Dec. 30, 2015.
(Continued)

*Primary Examiner* — Phillip Gray
(74) *Attorney, Agent, or Firm* — Nath, Goldberg & Meyer; Joshua B. Goldberg; Tanya E. Harkins

(57) ABSTRACT

An applicator of one aspect for applying a sheet member to skin includes a body having a bottom surface facing the skin and a first guide configured to guide the sheet member to a space between the skin and the bottom surface, in which the sheet member is applied to the skin after being folded in the space.

4 Claims, 19 Drawing Sheets

(51) Int. Cl.
   *A61M 35/00* (2006.01)
   *A61M 25/00* (2006.01)
   *A61M 25/02* (2006.01)
(52) U.S. Cl.
   CPC ..... *A61M 37/00* (2013.01); *A61M 2025/0266* (2013.01); *A61M 2037/0023* (2013.01)
(58) Field of Classification Search
   USPC .......................................................... 604/173
   See application file for complete search history.

(56) References Cited

U.S. PATENT DOCUMENTS

| | | | |
|---|---|---|---|
| 2003/0083645 A1* | 5/2003 | Angel ............... | A61M 5/14248 604/890.1 |
| 2004/0087992 A1 | 5/2004 | Gartstein et al. | |
| 2005/0112135 A1 | 5/2005 | Cormier et al. | |
| 2005/0245845 A1 | 11/2005 | Roe et al. | |
| 2006/0149297 A1 | 7/2006 | Sherman et al. | |
| 2007/0106207 A1 | 5/2007 | Withey | |
| 2008/0125743 A1 | 5/2008 | Yuzhakov | |
| 2010/0168638 A1 | 7/2010 | Korogi et al. | |
| 2010/0262081 A1 | 10/2010 | Lee et al. | |

FOREIGN PATENT DOCUMENTS

| | | |
|---|---|---|
| GB | 2 448 493 A | 10/2008 |
| GB | 2480542 A | 11/2011 |
| JP | 3016317 U | 7/1995 |
| JP | 3049583 U | 4/1998 |
| JP | 10-290820 A | 11/1998 |
| JP | 2001-61894 A | 3/2001 |
| JP | 2004-501726 A | 1/2004 |
| JP | 2005-503210 A | 2/2005 |
| JP | 2008-543528 A | 12/2008 |
| JP | 2017-820 A | 1/2017 |
| KR | 1020110092914 A | 8/2011 |
| WO | 02/02177 A1 | 1/2002 |
| WO | 2007/002522 A1 | 1/2007 |
| WO | 2008091878 A1 | 7/2008 |
| WO | 2012144437 A1 | 10/2012 |
| WO | 2013/038890 A1 | 3/2013 |
| WO | 2013/187392 A1 | 12/2013 |
| WO | 2014/203910 A1 | 12/2014 |

OTHER PUBLICATIONS

ISR issued in international application No. PCT/JP2014/066070 dated Sep. 22, 2014.
IPRP issued in international application No. PCT/JP2014/066068 dated Dec. 30, 2015.
European Search Report dated Feb. 15, 2017 in corresponding to European Patent Counterpart Application No. 14813654.2.
Office action in non-counterpart U.S. Appl. No. 14/899,148, dated Oct. 6, 2016.
European Search Report dated Feb. 7, 2017 issued in corresponding European Application No. EP14814482.7.
Notice of Allowance dated May 31, 2017 issued in corresponding Korean Application No. 10-2016-7000284.
Office Action dated Apr. 3, 2017 issued in U.S. Appl. No. 14/407,258.
Office Action dated Apr. 7, 2017 issued in U.S. Appl. No. 14/916,354.
Office Action dated May 19, 2017 issued in corresponding Chinese Application No. 201480034452.X.
Extended European Search Report dated Mar. 28, 2017 corresponding to application No. 14843133.1-1501.
Office Action dated Sep. 22, 2017 in non-counterpart U.S. Appl. No. 14/899,148.

* cited by examiner

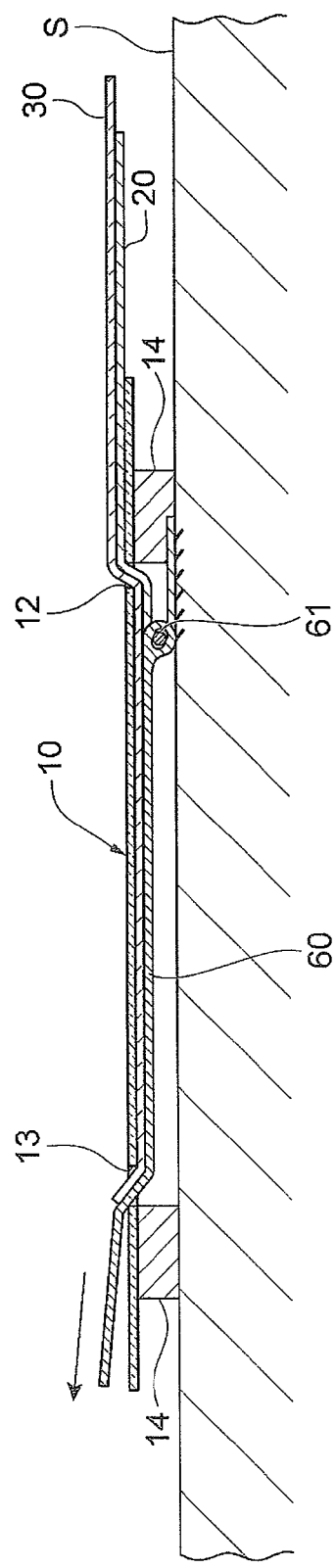

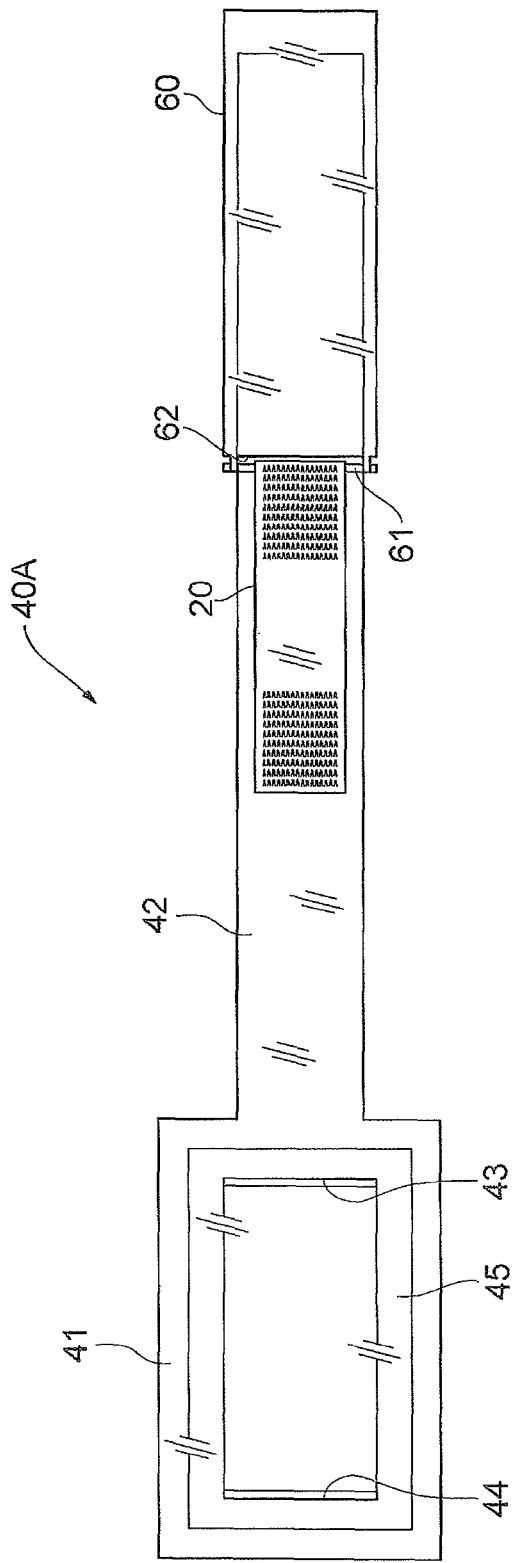

APPLICATOR

This is a National Phase Application filed under 35 U.S.C. 371 as a national stage of PCT/JP2014/066070, filed Jun. 17, 2014, an application claiming the benefit of Japanese Application No. 2013-127492, filed Jun. 18, 2013, and Japanese Application No. 2013-128624, filed Jun. 19, 2013, the content of each of which is hereby incorporated by reference in its entirety.

TECHNICAL FIELD

An aspect of the present invention relates to an applicator used for assisting in administration of an active component.

BACKGROUND ART

Sheet members are conventionally known for administering active components through skin. Examples include a patch disclosed in Patent Literature 1 below and a microneedle sheet as shown in FIG. 1 of the present application. Instruments for assisting in affixing a seat member are also known. Patent Literature 1 discloses an auxiliary implement for patch application. This auxiliary implement includes a backing having a surface larger than a patch, wherein on one surface of the backing there are provided an adhesive surface portion which is coated with a pressure-sensitive adhesive and serves for temporarily and peelably holding the patch, and a non-adhesive surface portion.

CITATION LIST

Patent Literature

[Patent Literature 1] WO2002/002177

SUMMARY OF INVENTION

Technical Problem

Unfortunately, when the auxiliary implement disclosed in Patent Literature 1 is used, it may be difficult to remove the peeling sheet after the patch is held on the adhesive surface portion of the backing, because the adhesive surface portion is generally flat. For this problem, the patch may be held on the adhesive surface portion of the auxiliary implement after the peeling sheet is peeled from the patch. In this case, however, the adhesive layer of the patch may stick together or creases may occur due to flexibility of the patch.

In the microneedle sheet shown in FIG. 1, since a plurality of microneedles are formed along the main surface of the sheet, the microneedles have to be raised from the main surface in order to insert these microneedles into skin.

As described above, requirements vary according to kinds of sheet members. It is then convenient if an applicator capable of applying different kinds of sheets to skin appropriately is provided.

Solution to Problem

According to an aspect of the present invention, an applicator for applying a sheet member to skin is provided. The applicator includes a body having a bottom surface facing the skin and a first guide configured to guide the sheet member to a space between the skin and the bottom surface. The sheet member is applied to the skin after being folded in the space.

In this aspect, the sheet member is guided between the skin and the bottom surface of the applicator and folded in that space, and thereafter applied to the skin. As described above, a mechanism that bends the sheet member in the space between the bottom surface of the applicator body and the skin can be employed to apply different kinds of sheet members to the skin appropriately. For example, in the case of a patch, the release sheet can be removed from the adhesive layer of the patch upon bending of the patch, and then the adhesive layer can be applied to the skin. In the case of a microneedle sheet, the microneedles can be raised from the main surface of the sheet upon bending of the microneedle sheet and applied to the skin.

The applicator according to another aspect may further include a second guide. The first guide may guide the sheet member provided on a liner to the space, and the second guide may guide the liner to the outside of the space.

In the applicator according to another aspect, the body may be shaped like a sheet.

In the applicator according to another aspect, both of the first guide and the second guide may be slit-shaped holes.

In the applicator according to another aspect, one end of the liner may be connected with one end of the body.

In the applicator according to another aspect, the first guide may be a first edge of the body, and the second guide may be a second edge facing the first edge.

In the applicator according to another aspect, an auxiliary liner including a cylindrical member may be attached to the liner, the sheet member may be attached to the auxiliary liner such that one end of the sheet member surrounds the cylindrical member, and the sheet member may be folded by the cylindrical member in the space.

In the applicator according to another aspect, an adhesive layer may be provided on at least part of the bottom surface.

In the applicator according to another aspect, at least part of the bottom surface may be elevated.

In the applicator according to another aspect, the sheet member may be a microneedle sheet having a plurality of microneedles formed along a main surface of the sheet.

Advantageous Effects of Invention

According to an aspect of the present invention, different kinds of sheet members can be applied to skin appropriately.

BRIEF DESCRIPTION OF DRAWINGS

FIG. 18 is a diagram schematically illustrating exemplary application of the microneedle sheet shown in FIG. 17.

FIG. 19 is a plan view of an applicator according to a modification.

DESCRIPTION OF EMBODIMENTS

Embodiments of the present invention will be described in details below with reference to the accompanying drawings. In the description of the drawings, the same or equivalent components are denoted with the same reference signs and an overlapping description will be omitted.

First Embodiment

An applicator 10 according to a first embodiment is an assist device used when a sheet member for administering any given active component (for example, drugs) into a living body is applied to skin. Sheet members that can be used with the applicator 10 and applied to skin are not specifically limited. Examples of the sheet member include patches (transdermal patches) and microneedle sheets. In the present embodiment, the applicator 10 is used for applying a microneedle sheet to skin, by way of example. In the example described below, the user can use the applicator 10 to insert microneedles into skin with more appropriate force than when bending the microneedle sheet directly by hand.

Figure 1:
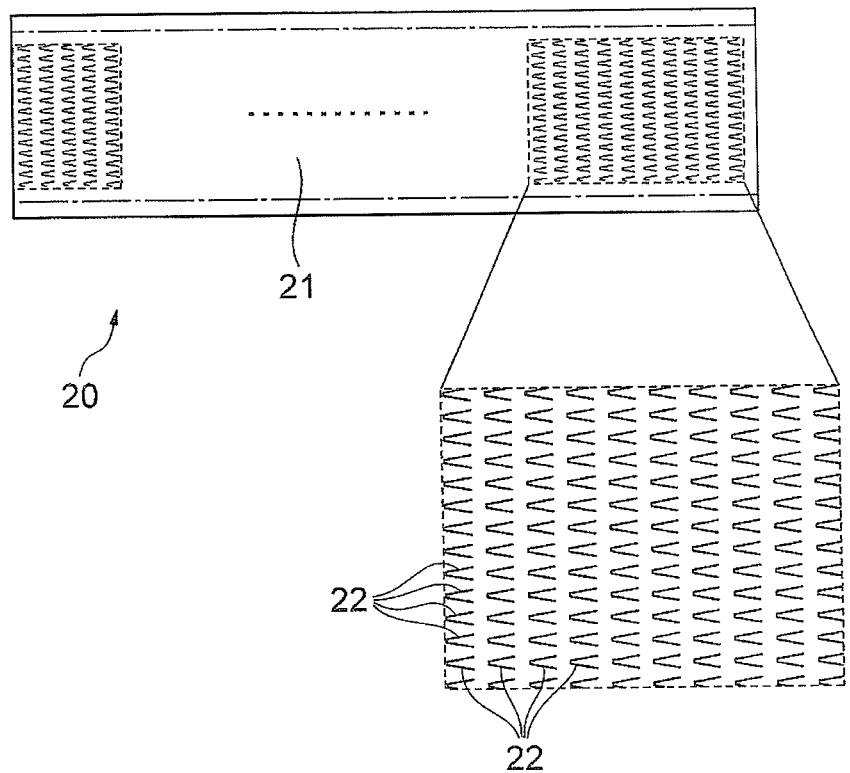
FIG. 1 is a plan view of a microneedle sheet used with an applicator according to an embodiment.

First, a microneedle sheet 20 used with the applicator 10 will be described. As shown in FIG. 1, the microneedle sheet 20 is shaped like a strip and has a plurality of microneedles 22 formed on the sheet generally along the main surface 21 of the sheet. These microneedles 22 are arranged in alignment with each of the longitudinal direction and the width direction of the sheet. The tip ends of all of the microneedles 22 are oriented toward one end of the sheet (leftward in FIG. 1) without exception.

The microneedle sheet 20 and the microneedles 22 are of any material. For example, the microneedle sheet 20 and the microneedles 22 may be made from any one of stainless steel, polyethylene terephthalate (PET), other metals, other resins, biodegradable materials, ceramics, and bioabsorbable materials. Alternatively, the microneedle sheet 20 and the microneedles 22 may be made from these materials in combination.

The microneedles 22 can be formed by etching. If the sheet is metallic, the microneedles 22 can be formed by etching the sheet by chemicals. If the sheet is non-metallic, the microneedles 22 can be formed by cutting the sheet by laser. In these cases, a gap is produced on the periphery of the microneedles 22. It is needless to say that the microneedles 22 can be formed by any technique other than etching. Although the microneedles 22 are each triangular in the present embodiment as shown in FIG. 1, the microneedles may have any shape. In any case, the microneedle sheet 20 can be produced readily and inexpensively because there is no need for raising the microneedles 22 from the main surface 21 of the sheet in advance.

The microneedle sheet 20 may be of any size. Specifically, the lower limit of the thickness may be 5 μm or 20 μm, and the upper limit of the thickness may be 1000 μm or 300 μm. The lower limit of the length may be 0.1 cm or 1 cm, and the upper limit of the length may be 50 cm or 20 cm. The lower limit of the width may be 0.1 cm or 1 cm, and the upper limit of the width may be 60 cm or 30 cm. The lower limits of the length and the width of the microneedle sheet 20 are determined considering the dose of active components, and the upper limits of the length and the width may be determined considering the size of the living body.

Parameters pertaining to the microneedles 22 may also have any value. Specifically, the lower limit of the height of each needle may be 10 μm or 100 μm, and the upper limit of the height may be 10000 μm or 1000 μm. The lower limit of the density of needles may be 0.05 needle/cm$^2$ or 1 needle/cm$^2$, and the upper limit of the density may be 10000 needles/cm$^2$ or 5000 needles/cm$^2$. The lower limit of the density is a value obtained in terms of the number of needles and area with which 1 mg of an active component can be administered. The upper limit of the density is a limit value in consideration of the shapes of the needles.

An active component to be applied to skin may be prepared by the following procedures: coating the microneedle sheet 20 per se with an active component in advance; applying an active component on skin before inserting the microneedles 22 into the skin; and inserting the microneedles 22 into skin and thereafter applying an active component on the skin. If the microneedle sheet 20 is coated with an active component in advance, it is preferable to apply a coating liquid having a predetermined viscosity at a thickness as uniform as possible over the entire sheet. Such application can be easily done because the microneedles 22 are arranged along the main surface 21. The coating may be carried out using the principles of screen printing or may be carried out by any other method. If a biodegradable sheet is used, an active component may be included in the sheet per se.

Figure 2:
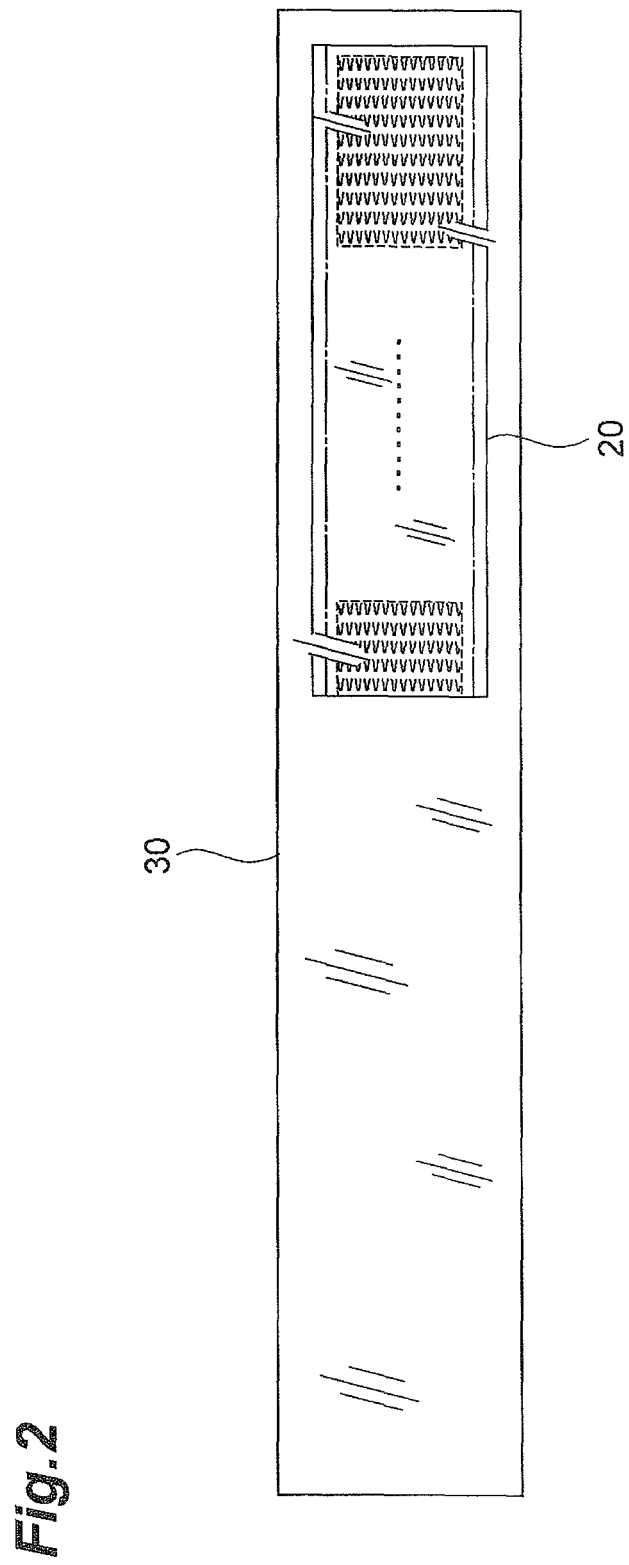
FIG. 2 is a diagram illustrating the microneedle sheet fixed to a liner.
Figure 3:
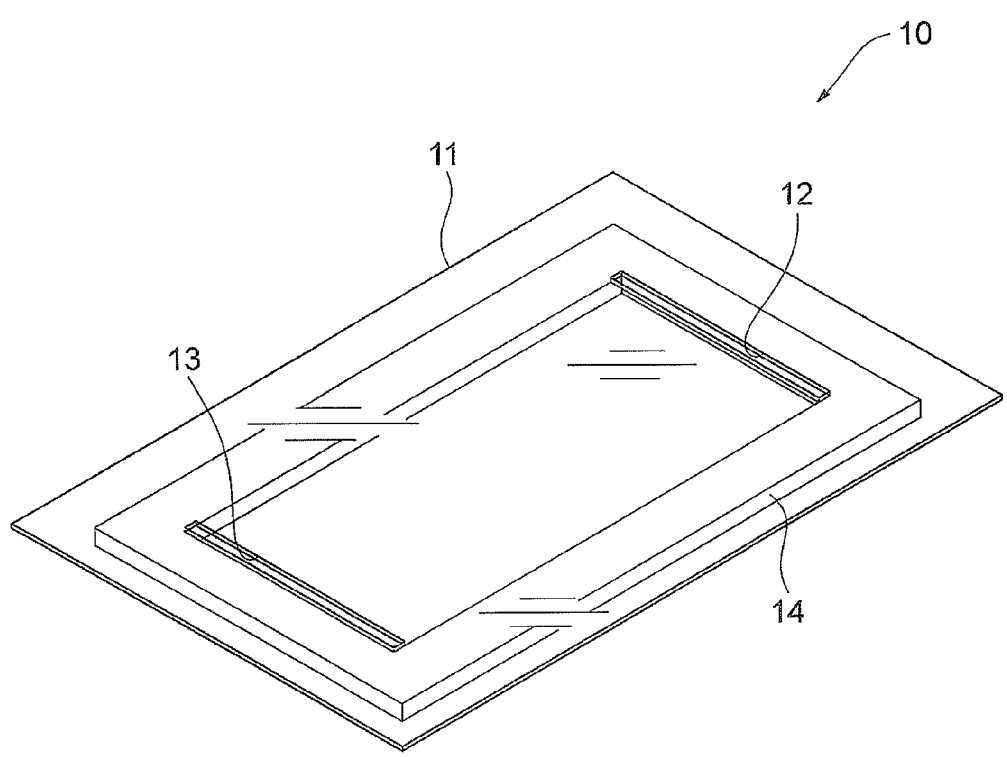
FIG. 3 is a perspective view of an applicator according to a first embodiment.
Figure 4:
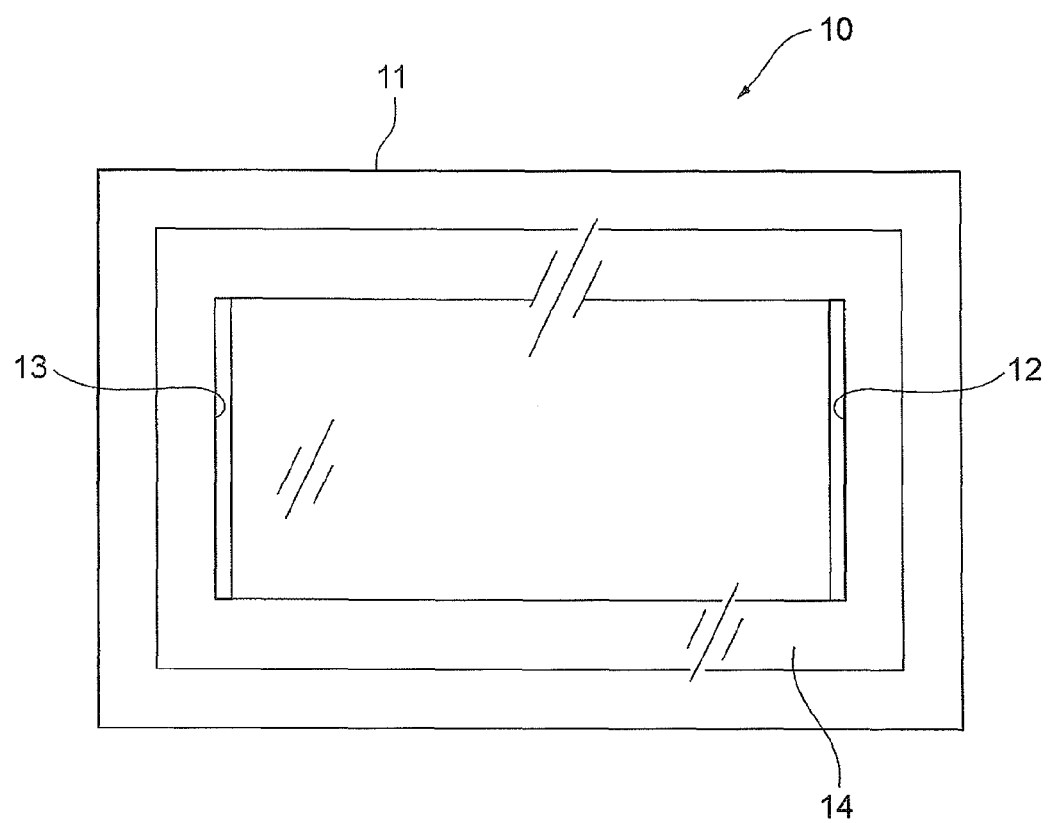
FIG. 4 is a plan view corresponding to FIG. 3.
Figure 5:
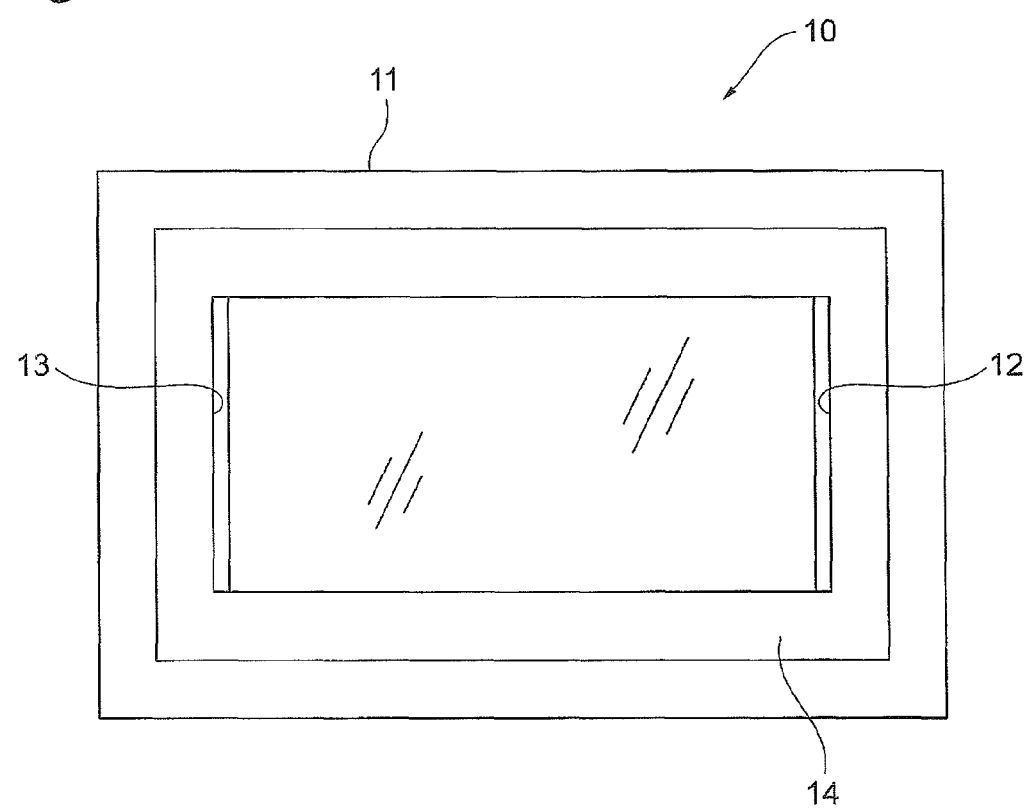
FIG. 5 is a bottom view corresponding to FIG. 3.

In the present embodiment, a liner 30 is used for setting the microneedle sheet 20 in the applicator 10. As shown in FIG. 2, this liner 30 is a strip-like sheet having a length and a width larger than those of the microneedle sheet 20. Examples of the material of the liner 30 include plastics such as acrylics. The liner 30, however, may be made from any material, for example, using a metal or any other resin. The microneedle sheet 20 is fixed to one end side of the liner 30 with tape, adhesive, or other means.

Although examples of the material of the liner 30 include plastics such as acrylics, the liner 30 may be made from any material, for example, using a metal or any other resin. Although the liner 30 illustrated in the related drawings is a transparent or translucent substance, the liner 30 may be opaque.

Figure 6:
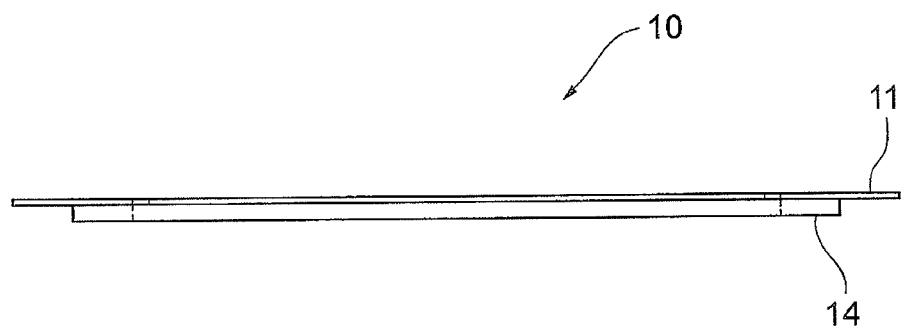
FIG. 6 is a front view (or a rear view) corresponding to FIG. 3.
Figure 7:
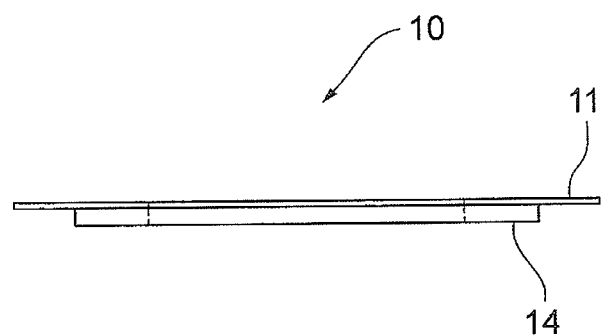
FIG. 7 is a right side view (or a left side view) corresponding to FIG. 3.

Referring now to FIGS. 3 to 7, a structure of the applicator 10 will be described. The applicator 10 is a rectangular sheet-like device. In the present embodiment, the side illustrated in FIG. 4 (plan view) is defined as the top side of the applicator 10, and the side illustrated in FIG. 5 (bottom view) is defined as the bottom side of the applicator 10. The appearances viewed from the front surface and from the rear surface of the applicator 10 are identical, and the appearances viewed from both side surfaces are also identical. FIG. 6 is therefore either a front view or a rear view of the applicator 10. FIG. 7 is either a right side view or a left side view of the applicator 10.

The body 11 of the applicator 10 has two slit-shaped through holes formed along the direction orthogonal to the longitudinal direction (hereinafter referred to as "width direction"). One of the through holes is a hole for guiding the liner 30 and the microneedle sheet 20 from the top side to the bottom side of the body 11 and will hereinafter be referred to as first through hole 12. The other through hole is a hole for guiding the liner 30 stripped from the microneedle sheet 20 from the bottom side to the top side of the body 11 and will hereinafter be referred to as second through hole 13. The distance between the two through holes 12 and 13 may be determined considering the range of application of the microneedle sheet 20 to skin or may be determined considering other criteria.

On the bottom surface of the body 11, an adhesive (adhesive layer) 14 is provided in a rectangular shape so as to surround the two through holes 12 and 13. The adhesive 14 serves the function of fixing the applicator 10 on skin. The adhesive 14 may be provided in any range. For example, the adhesive 14 may be provided only along both edge portions in the longitudinal direction of the body 11 or may be provided only along both edge portions in the width direction of the body 11.

Examples of the material of the body 11 include plastics such as acrylics. The body 11, however, may be made from any material, for example, using a metal or any other resin. Although the body 11 illustrated in the related drawings is a transparent or translucent substance, the body 11 may be opaque.

The size of the applicator 10 may be determined in accordance with the size of the microneedle sheet 20 or the liner 30. For example, the width of the applicator 10 may be determined in accordance with the width of the liner 30. The entire length (the length along the longitudinal direction) of the applicator 10 may be determined considering the length of the microneedle sheet 20 or the range of application of the microneedle sheet 20 to skin.

Figure 8:
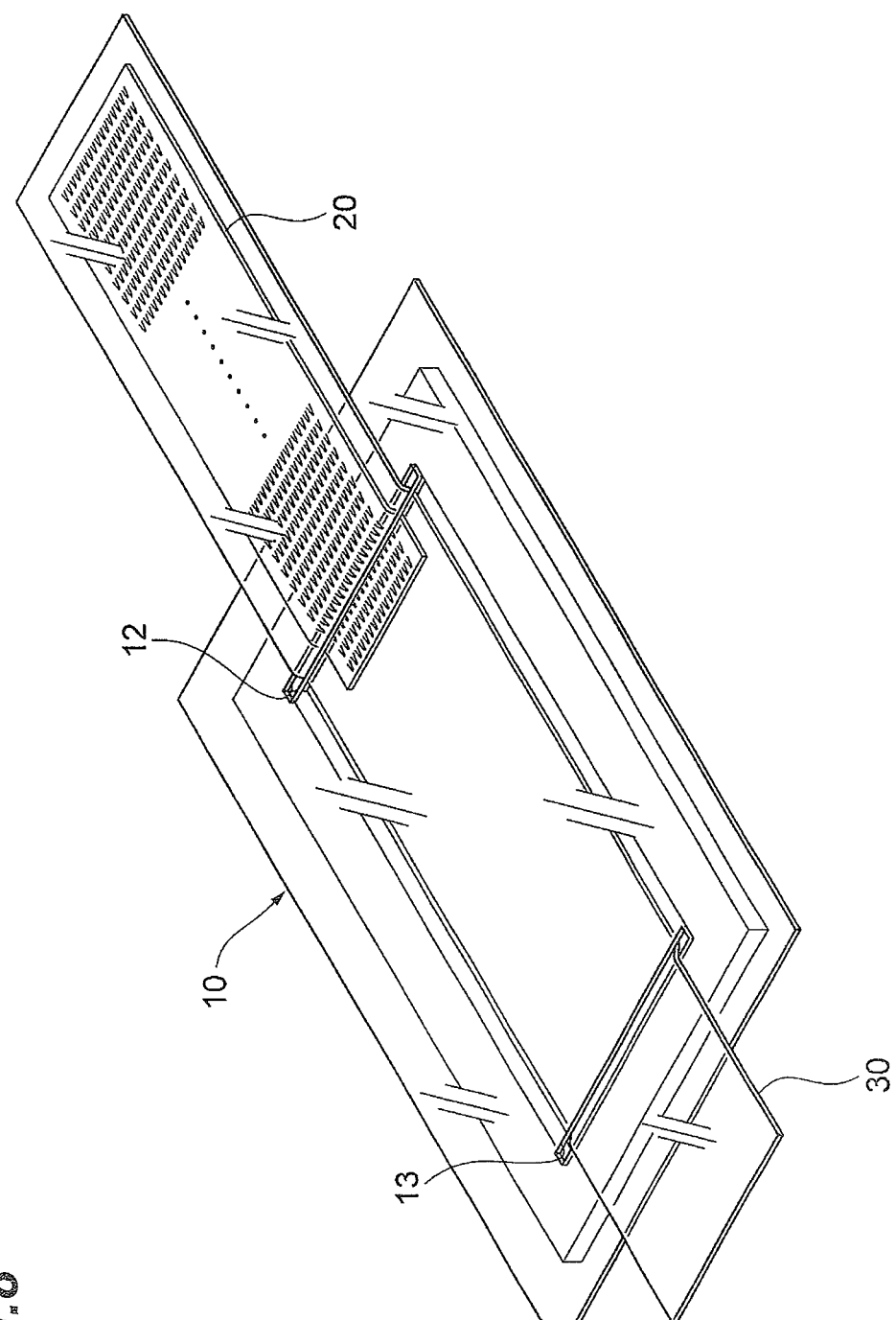
FIG. 8 is a diagram illustrating the usage of the applicator according to the first embodiment.

Referring now to FIGS. 8 to 11, the usage of the applicator 10 and the microneedle sheet 20 will be described. First, the user sets the liner 30 with the microneedle sheet 20 attached thereto, in the applicator 10. Specifically, the user passes one end of the liner 30 on which the microneedle sheet 20 is not fixed through the first through hole 12 from above to below and further passes the one end through the second through hole 13 from below to above. With this preparation, the liner 30 is positioned on the bottom surface side of the applicator 10 between the two through holes 12 and 13, as shown in FIG. 8.

Figure 9:
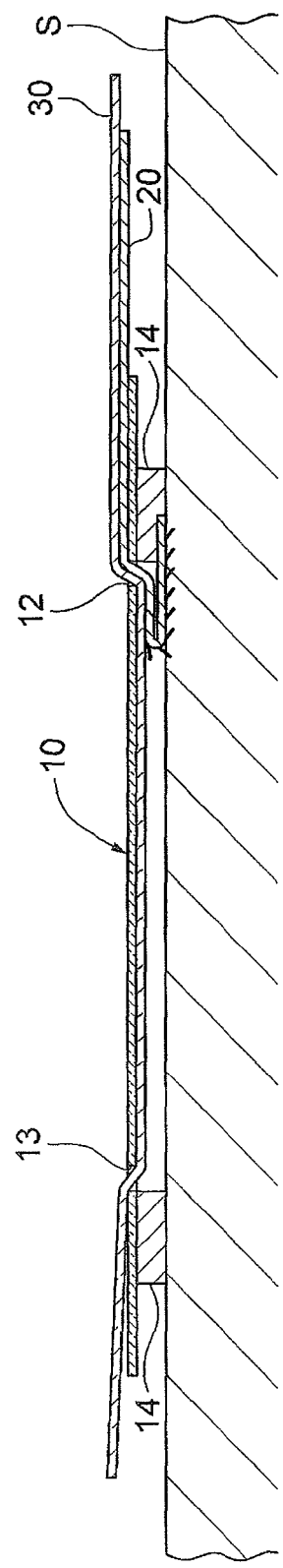
FIG. 9 is a diagram schematically illustrating application of the microneedle sheet.

The user then draws one end of the microneedle sheet 20 from the first through hole 12 to the bottom surface side of the applicator 10 and folds the one end such that the one end is positioned below the adhesive 14. Keeping this state, the user affixes the applicator 10 to a site of application of an active component. Through a series of these operations, the applicator 10 is fixed on skin S as shown in FIG. 9.

Figure 10:
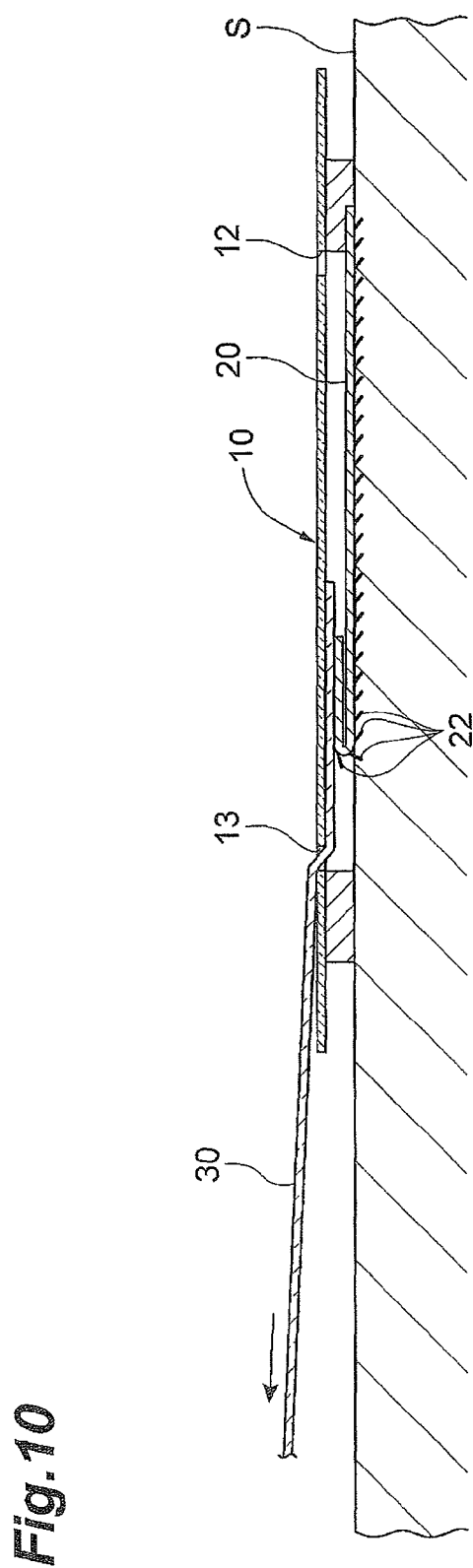
FIG. 10 is a diagram schematically illustrating application of the microneedle sheet.

The user then pulls one end of the liner 30 in the direction denoted by the arrow in FIG. 10. Through this operation, the microneedle sheet 20 is guided by the liner 30 to pass through the first through hole 12 and enter the space between the skin S and the bottom surface of the applicator 10.

Figure 11:
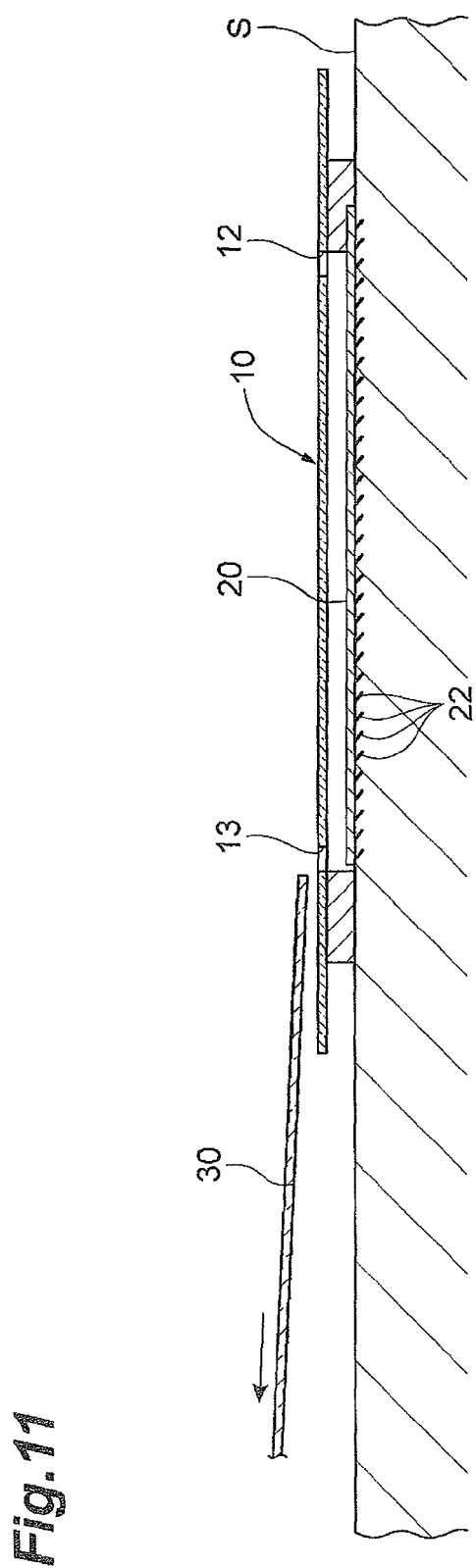
FIG. 11 is a diagram schematically illustrating application of the microneedle sheet.

The microneedle sheet 20 is bent by 180 degrees in this space. As shown in FIG. 10, the microneedles 22 located at the bent portion are then raised from the main surface 21, and the raised microneedles 22 stick into the skin S. The user pulls the liner 30 until the entire liner 30 is pulled out of the applicator 10, so that the entire microneedle sheet 20 is applied to the skin as shown in FIG. 11.

The user thereafter can remove the applicator 10 from the skin. The user may remove the microneedle sheet 20 immediately or may keep the microneedle sheet 20 applied on the skin S over a predetermined time. In the present embodiment, the microneedle sheet 20 is fixed to the liner 30 with tape or adhesive, and the tape or adhesive can also be used for fixing the microneedle sheet 20 on the skin.

A row of microneedles 22 along the width direction of the microneedle sheet 20 are raised at a time between the applicator 10 and the skin S. The angle between the raised microneedle 22 and the main surface 21 is greater than 0 degrees and less than 180 degrees, as a matter of course.

Figure 12:
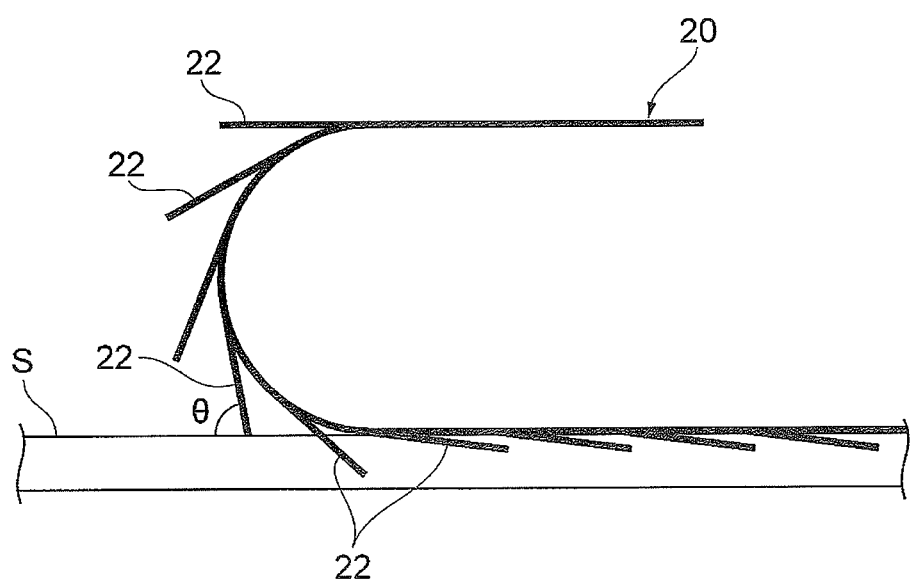
FIG. 12 is a diagram schematically illustrating a manner of puncture.

As shown in FIG. 12, the angle θ of insertion (the angle between the microneedle 22 and the skin S) during insertion of the microneedle 22 raised from the main surface 21 into skin is also greater than 0 degrees and less than 180 degrees. The lower limit of the angle of insertion may be 20 degrees, 34 degrees, or 40 degrees, and the upper limit of the angle of insertion may be 160 degrees, 140 degrees, or 100 degrees.

As described above, according to the present embodiment, the microneedle sheet 20 is guided between the skin and the bottom surface of the applicator 10, folded such that the active surface of the sheet 20 (the surface from which the microneedles 22 are raised) faces the outside of the arc, and then applied to skin.

As described above, this applicator 10 can also be used for application of a patch. First, the user affixes a patch to the liner 30 with the adhesive layer exposed. Alternatively, the patch may be affixed to the liner 30 in advance. In this case, the liner 30 serves the function of a release sheet for the patch. The user then passes the liner 30 through the two through holes 12 and 13 in the same manner as described above, then fixes the applicator 10 on skin, and pulls the liner 30. Through this operation, the patch is guided to the space between the skin and the bottom surface of the body 11 and folded such that the adhesive layer (the active surface of the patch) faces the outside of the arc to stick to the skin.

As described above, the applicator 10 can apply different kinds of sheet members to skin appropriately.

In the present embodiment, the applicator 10 includes the first through hole 12 for guiding the liner with the sheet member to the surface of skin and the second through hole 13 for guiding the liner stripped from the sheet member to the outside of the applicator 10. The provision of such two through holes facilitates, for example, peeling of the liner from the sheet member and application of the sheet member to skin without causing wrinkles.

In the present embodiment, the body 11 of the applicator 10 is shaped like a sheet and therefore is considerably small in size in the height direction. The applicator 10 thus has great portability. Even when fixed on skin together with the sheet member for a certain long time, the applicator 10 hardly interferes with the movement of the subject nor gives uncomfortable feeling to the subject.

In the present embodiment, since the adhesive 14 is provided on the bottom surface of the applicator 10, the user can fix the applicator 10 on skin without using another member such as tape.

In the present embodiment, the applicator 10 inserts each needle 22 into skin by raising the microneedles 22 and pushing the raised microneedles 22 into skin, rather than giving impact to the microneedle sheet 20. The active component therefore can be administered to the subject without causing a sense of fear.

When it comes to the microneedle sheet 20, the microneedles 22 lie generally along the main surface 21 of the sheet until the microneedle sheet 20 is bent. There is therefore no concern that the microneedles 22 touch or get caught in other objects (for example, the user's skin or clothes) unless the applicator 10 is used. As a result, the safety in handling the microneedles 22 can be ensured. For example, the user can safely carry out storage and conveyance of the microneedle sheet 20 or make preparations immediately before use.

Second Embodiment

A structure of an applicator 40 according to a second embodiment will now be described. In the following, the configuration different from the first embodiment will be specifically described and the description of the same configuration as in the first embodiment will be omitted.

Figure 13:
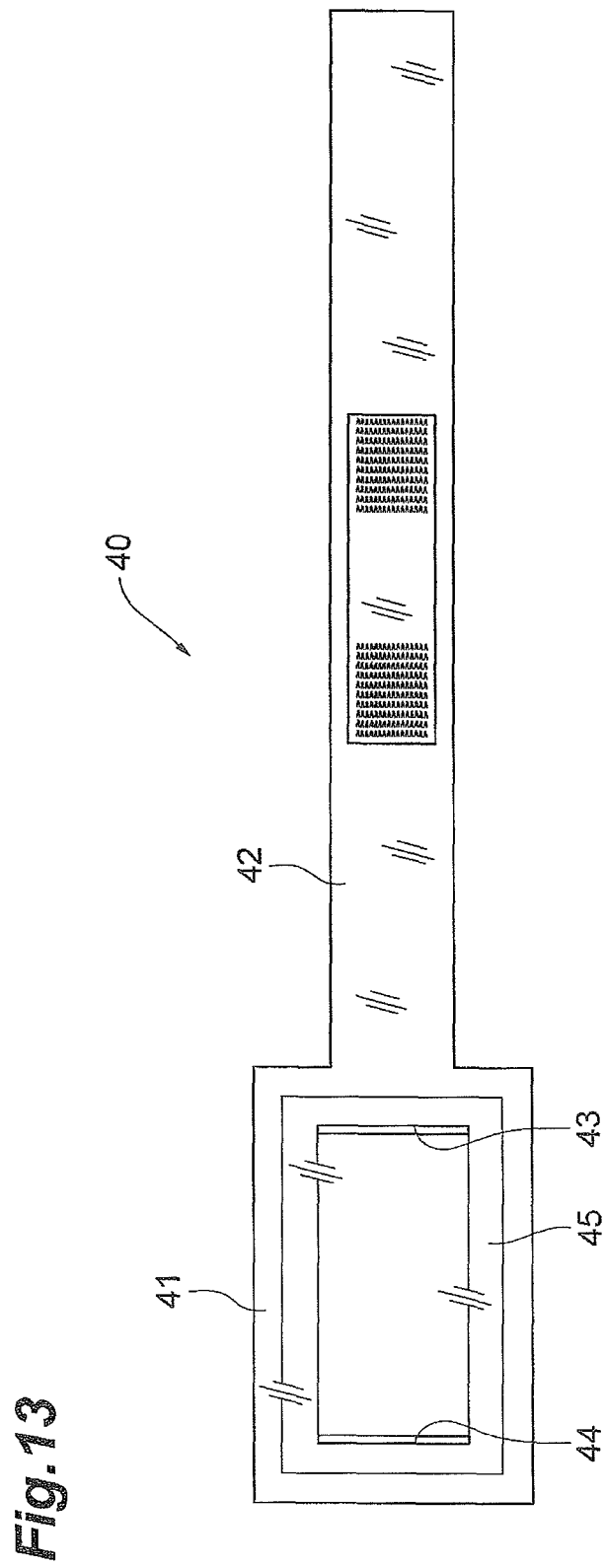
FIG. 13 is a plan view of an applicator according to a second embodiment.

As shown in FIG. 13, the applicator 40 includes a rectangular body 41 and a liner 42 connected to the body 41 at one end in the longitudinal direction of the body 41. It is therefore can be said that the applicator 40 is formed by integrating the applicator 10 and the liner 30 in the first embodiment.

The structure of the body 41 is the same as the applicator 10 in the first embodiment. The body 41 has two slit-shaped through holes each formed along its width direction. One of the through holes that is closer to the liner 42 is a first through hole 43 for guiding the liner 42 and the microneedle sheet 20 from the top side to the bottom side of the body 41. The other through hole is a second through hole 44 for guiding the liner 42 stripped from the microneedle sheet 20 from the bottom side to the top side of the body 41. On the bottom surface of the body 41, an adhesive (adhesive layer) 45 is provided in a rectangular shape so as to surround the two through holes 43 and 44.

The structure of the liner 42 is the same as the liner 30 in the first embodiment. The liner 42 has a length sufficient to apply the microneedle sheet 20 to skin through a series of operations described later. The width of the liner 42 is smaller than the width of each of the through holes 43 and 44. The microneedle sheet 20 is fixed in the vicinity of the center on the top surface of the liner 42 with tape or adhesive in the same manner as in the first embodiment.

Figure 14:
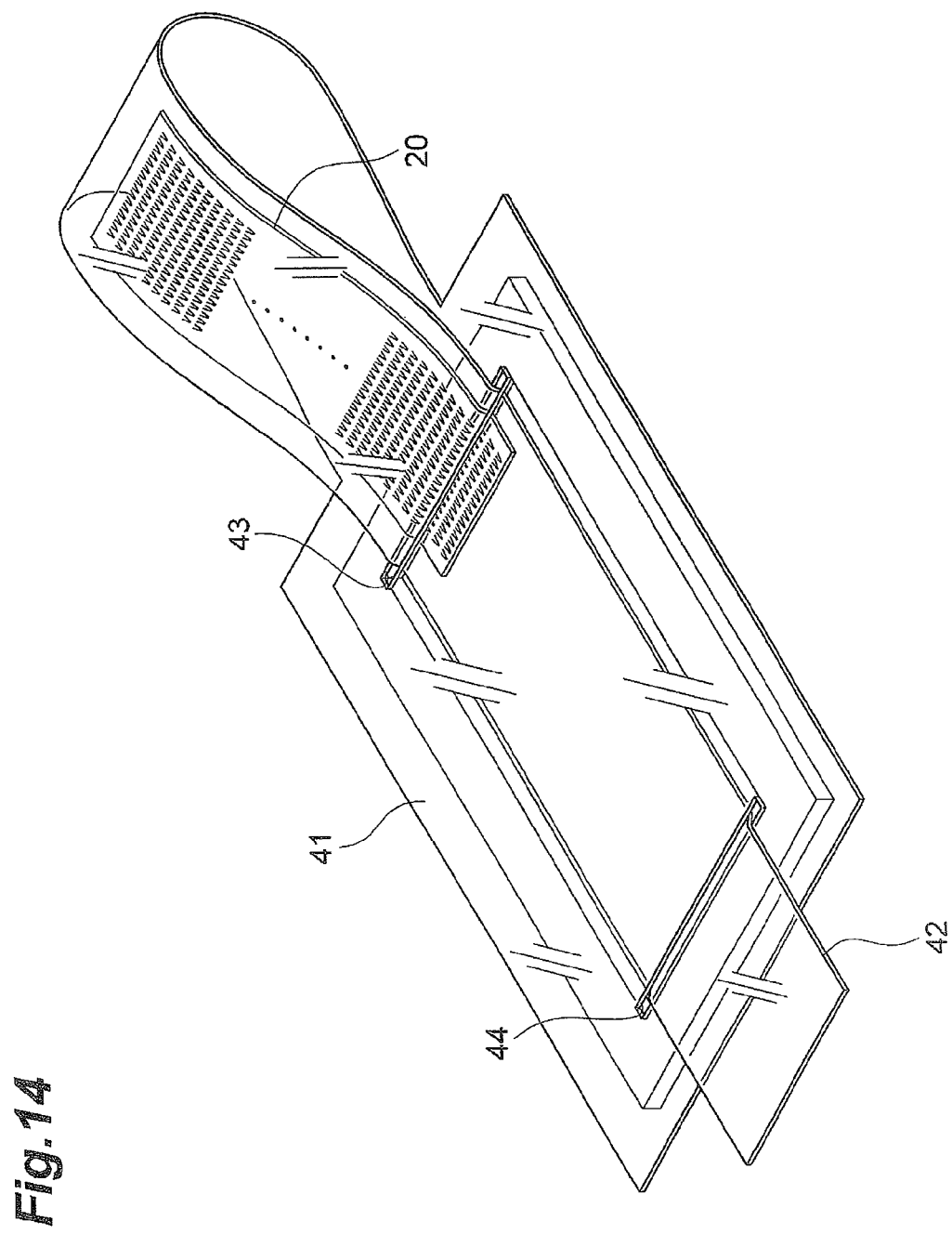
FIG. 14 is a diagram illustrating the usage of the applicator according to the second embodiment.

Referring now to FIG. 14, the usage of the applicator 40 and the microneedle sheet 20 will be described. First, the user passes one end of the liner 42 on which the microneedle sheet 20 is attached through the first through hole 43 from above to below and further passes the one end through the second through hole 44 from below to above. With this preparation, part of the liner 42 is positioned on the bottom surface side of the applicator 40 between the two through holes 43 and 44, as shown in FIG. 14.

The subsequent operation of the applicator 40 is the same as in the first embodiment. That is, the user draws one end of the microneedle sheet 20 from the first through hole 43 to the bottom surface side of the applicator 40 and folds the one end so that the one end is positioned below the adhesive 45. Keeping this state, the user affixes the applicator 40 to a site of application of an active component (in the same manner as in FIG. 9). The user then pulls one end of the liner 42. Through this operation, the microneedle sheet 20 guided to the space between the skin and the bottom surface of the applicator 40 is bent by 180 degrees. The microneedles 22 located at the bent portion are then raised from the main surface 21 of the sheet, and the raised microneedles 22 stick into skin S (in the same manner as in FIG. 10). The user pulls the liner 42 until the entire microneedle sheet 20 is applied to the skin (in the same manner as in FIG. 11).

Also in the second embodiment as described above, a sheet member such as the microneedle sheet 20 or a patch can be applied to skin appropriately by the same mechanism as in the first embodiment. The operation for applying a patch is as follows. First, the user affixes a patch to the liner 42 with the adhesive layer exposed. Alternatively, the patch may be affixed to the liner 42 in advance. In this case, the liner 42 serves the function of a release sheet for the patch. The user then passes the liner 42 through the two through holes 43 and 44 in the same manner as described above, then fixes the applicator 40 on skin, and pulls one end of the liner 42. Through this operation, the patch is guided to the space between the skin and the bottom surface of the body 41 and folded such that the adhesive layer (the active surface of the patch) faces the outside of the arc in that space and sticks to the skin.

The effects obtained by the provision of the two through holes 43 and 44, the effects obtained by the sheet-like shape of the applicator 40, and the effects obtained by the provision of the adhesive 45 are also the same as in the first embodiment. An active component can be administered to the subject without causing a sense of fear in the same manner as in the first embodiment.

In the present embodiment, the body 41 is integrated with the liner 42. With this configuration, the user pulls the liner 42 to apply the microneedle sheet 20 to the skin and then keeps pulling the liner 42, so that the body 41 is removed from the skin staring from the end connected to the liner 42. The user therefore merely requires a single operation of pulling the liner 42 to apply the microneedle sheet 20 to skin and to strip the applicator 40 from the skin.

The present invention has been described in details above based on the embodiments. The present invention, however, is not intended to be limited to the foregoing embodiments. The present invention is susceptible to various modifications without departing from the gist of the invention.

Figure 15:
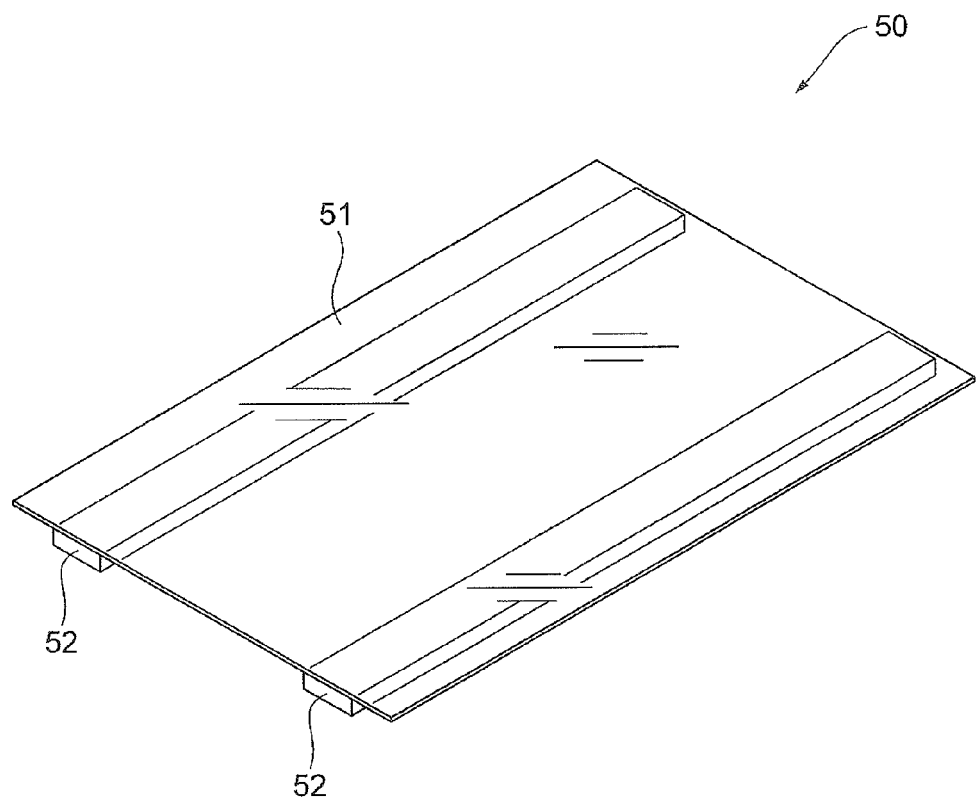
FIG. 15 is a perspective view of an applicator according to a modification.

An applicator 50 without a through hole as shown in FIG. 15 is included in the scope of the present invention. In the applicator 50, the body 51 does not have a through hole. Instead, adhesives 52 are provided over both edge portions along the longitudinal direction. The distance between the two adhesives 52 is greater than the width of the liner 30. In this applicator 50, both edge portions in the longitudinal direction of the body 51 function as first and second guides.

The user can use the microneedle sheet 20 (the same as the first embodiment) fixed to the liner 30 and this applicator 50 to insert the microneedles into skin.

Figure 16:
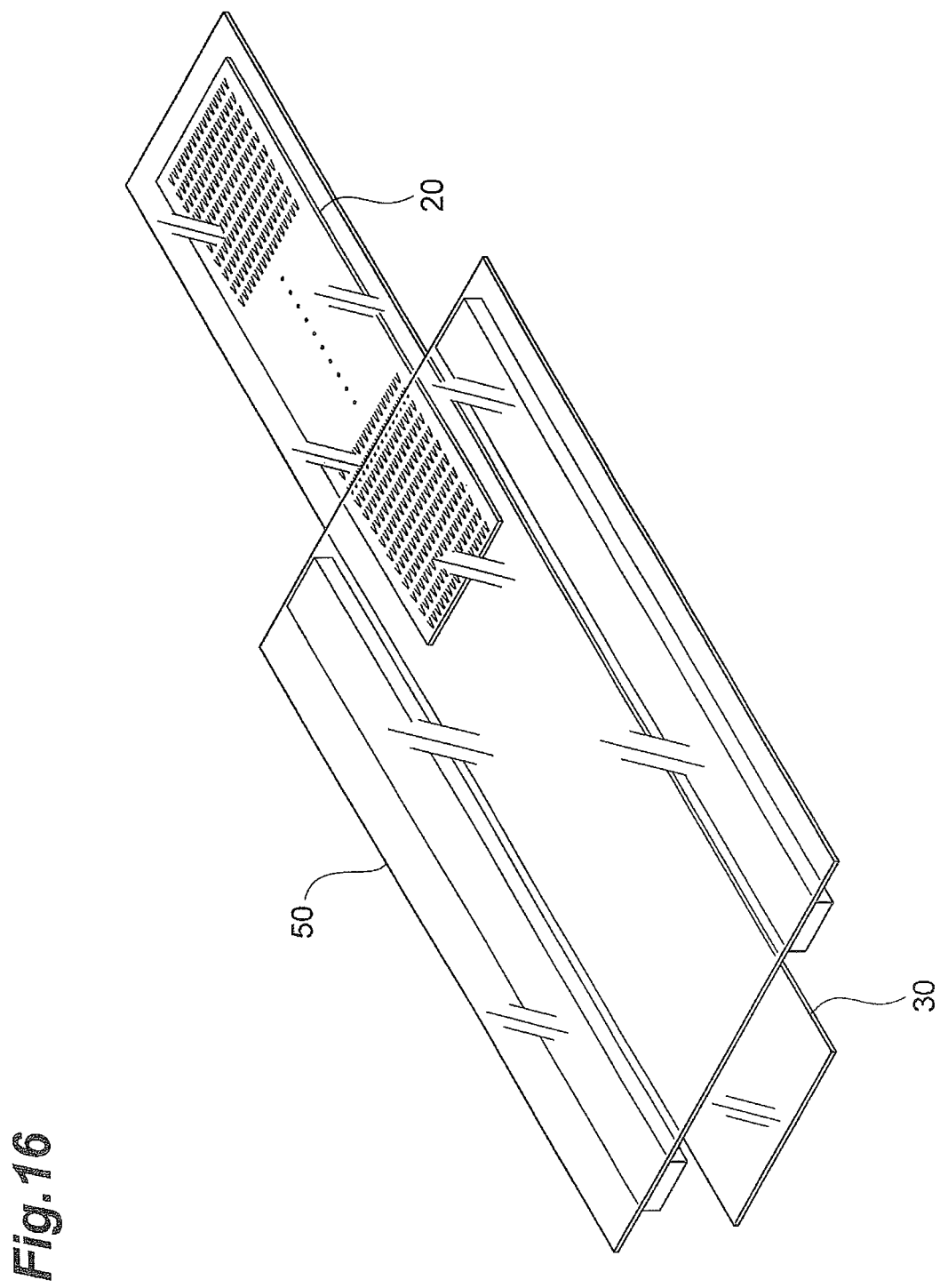
FIG. 16 is a diagram illustrating the usage of the applicator according to the modification.

As shown in FIG. 16, the user arranges the liner 30 on the bottom surface side of the applicator 50 such that the part of the liner 30 to which the microneedle sheet 20 is not fixed is positioned between the two adhesives 52. The user then folds one end of the microneedle sheet 20 and, keeping this state, affixes the applicator 50 to a site of application of an active component (in the same manner as in FIG. 9).

The subsequent procedure is the same as in the first embodiment. That is, the user pulls one end of the liner 30, so that the microneedle sheet 20 is guided to the space between the skin and the bottom surface of the body 51. Through this operation, the microneedle sheet 20 is drawn into the space, and the microneedle sheet 20 is bent by 180 degrees in that space. The microneedles 22 located at the bent portion are then raised from the main surface 21 of the sheet, and the raised microneedles 22 stick into the skin S (in the same manner as in FIG. 10). The user pulls the liner 30 until the entire microneedle sheet 20 is applied to the skin (in the same manner as in FIG. 11).

The applicator 50 can also be used for applying any given sheet member, as a matter of course. The operation for applying a patch is as follows. First, the user affixes a patch to the liner 30 with the adhesive layer exposed. Alternatively, the patch may be affixed to the liner 30 in advance. In this case, the liner 30 serves the function of a release sheet for the patch. The user then arranges the liner 30 on the bottom surface side of the applicator 50 such that the liner 30 is positioned between the two adhesives 52, in the same manner as described above. The user then folds one end of the patch and, keeping this state, affixes the applicator 50 to a site of application of an active component (in the same manner as in FIG. 9). The user then pulls one end of the liner 30. Through this operation, the patch is guided to the space between the skin and the bottom surface of the body 51 and folded such that the adhesive layer (the active surface of the patch) faces the outside of the arc to stick to the skin.

The body of the applicator may not be shaped like a sheet. The applicator may have any height.

The provision of an adhesive layer on the bottom surface of the body is not essential. Even without an adhesive, the user can apply the microneedle sheet to skin through the same procedure as in the foregoing embodiments by holding the applicator by hand or other means or affixing the applicator to skin with tape.

At least one protrusion may be provided on the bottom surface of the body of the applicator. The protrusion extends toward the skin and, therefore, the height of the space at the protrusion (the distance from the skin to the apex of the protrusion) is smaller than the height of the space at a part not provided with the protrusion (the distance from the skin to the bottom). One or more protrusions are provided between the first guide and the second guide. Each protrusion may be shaped like a rail extending from the first guide to the second guide (that is, extending along the direction in which the sheet member is moved). Alternatively, each protrusion may be shaped like a rail extending in parallel with the first and second guides (that is, extending in the direction orthogonal to the direction in which the sheet member is moved). Alternatively, mountain-shaped or pillar-shaped protrusions may be two-dimensionally formed on the bottom surface. The term "two-dimensionally" as used herein refers to a manner in which a plurality of protrusions are formed along the direction extending from the first guide to the second guide and a plurality of protrusions are formed along the direction parallel to the first and second guides.

Individual protrusions may have different heights. For example, when a plurality of rail-shaped protrusions extending from the first guide to the second guide are provided, a protrusion located inside may be higher than a protrusion located outside. When a plurality of rail-shaped protrusions extending in parallel with the first and second guides are provided, in each protrusion, the center of the protrusion may be higher than both ends of the protrusion. When a plurality of mountain-shaped or pillar-shaped protrusions are provided two-dimensionally, a protrusion located inside may be higher than a protrusion located outside. As described above, when a plurality of protrusions are provided, an individual protrusion may be arranged or fox such that a part located on the inside of the body is higher than a part located on the outside of the body, as viewed along the direction orthogonal to the direction in which the sheet member is moved.

Alternatively, the entire region of the bottom surface between the first guide and the second guide may be elevated so that the height of the space is reduced, in the same manner as when protrusions are provided.

The formation of protrusions or the elevation of the entire region of the bottom surface between the first guide and the second guide as described above are examples of elevation of at least part of the bottom surface toward the skin. The elevation of at least part of the bottom surface toward the skin as described above allows the sheet member to be pressed against the skin in the space, so that the sheet member can be applied to the skin more reliably. For example, individual microneedles can be inserted into skin more reliably.

The method of providing a sheet member used with the applicator 10 or 50 is not intended to be limited to the foregoing embodiments. A modification of the sheet member will now be described with reference to FIGS. 17 and 18. In this modification, in order to set the microneedle sheet 20 in the applicator 10 or 50, an auxiliary liner 60 is used in addition to the same linear 30 as in the first embodiment. The auxiliary liner 60 is a strip-like sheet having a width greater than the width of the microneedle sheet 20 and includes a cylindrical member 61. At least part of the auxiliary liner 60 may have a width equal to or smaller than the width of the microneedle sheet 20. The cylindrical member 61 is attached to one end in the longitudinal direction of the auxiliary liner 60 so as to extend along the width direction (the direction orthogonal to the longitudinal direction) of the auxiliary liner 60. In this case, the cylindrical member 61 may be attached so as to be able to rotate. A slit-shaped hole 62 for allowing the microneedle sheet 20 to pass through is formed between the cylindrical member 61 and one end of the auxiliary liner 60. Examples of the material of the auxiliary liner 60 include plastics such as acrylics. The auxiliary liner 60, however, may be made from any material, for example, using a metal or any other resin. The material of the cylindrical member 61 may be a metal or a plastic such as acrylic or any other resin.

The microneedle sheet 20 is fixed to one end side of the liner 30 with tape, adhesive, or other means, in the same manner as in the first embodiment. The auxiliary liner 60 is attached to the other end side of the liner 30 such that the cylindrical member 61 is connected with the microneedle sheet 20. In doing so, the surface of the auxiliary liner 60 and the surface of the liner 30 may be fixed to each other with tape, adhesive, or other means, or these surfaces may not be fixed to each other. The microneedle sheet 20 is set on the auxiliary liner 60 by passing one end of the microneedle sheet 20 located near the center of the liner 30 through the hole 62 and folding the one end of the microneedle sheet 20 by 180 degrees so as to surround the cylindrical member 61.

The method of using the microneedle sheet 20 (that is, the microneedle sheet 20 shown in FIG. 17) attached to the liner 30 and the auxiliary liner 60 together with the applicator 10 will now be described. First, the user passes the auxiliary liner 60 through the first through hole 12 from above to below and further passes the auxiliary liner 60 through the second through hole 13 from below to above. With this preparation, as shown in FIG. 18, the auxiliary liner 60 is positioned on the bottom surface side of the applicator 10 between the two through holes 12 and 13, and part of the liner 30 is also positioned on the bottom surface side. In this case, the user puts one end of the microneedle sheet 20 folded in the vicinity of the cylindrical member 61, for example, below the adhesive 14. Keeping this state, the user affixes the applicator 10 to a site of application of an active component. Through a series of these operations, the applicator 10 is fixed on the skin S.

The user then pulls the auxiliary liner 60 in the direction denoted by the arrow in FIG. 18. This operation allows the cylindrical member 61 to move toward the second through hole 13. This movement of the cylindrical member 61 allows the liner 30 and the microneedle sheet 20 to pass through the first through hole 12 and enter the space between the skin S and the bottom surface of the body 11. The microneedle sheet 20 is bent by 180 degrees in this space by the cylindrical member 61. The microneedles 22 located at the bent portion are then raised from the main surface 21, and the raised microneedles 22 stick into the skin S. The liner 30 pulled apart from the microneedle sheet 20 is guided through the second through hole 13 to the outside of the space. The user keeps pulling the auxiliary liner 60 to apply the entire microneedle sheet 20 to the skin. The user thereafter can remove the applicator 10 from the skin. The user may remove the microneedle sheet 20 immediately or may keep the microneedle sheet 20 applied on the skin S over a predetermined time.

The manner of using the auxiliary liner 60 having the cylindrical member 61 is applicable when any sheet member is applied, as a matter of course. The operation for applying a patch is as follows. First, the user affixes a patch to the liner 30 with the adhesive layer exposed. Alternatively, the patch may be affixed to the liner 30 in advance. In this case, the liner 30 serves the function of a release sheet for the patch. The user then passes the auxiliary liner 60 through the two through holes 12 and 13 in the same manner as described above. The user then puts an end of the patch folded in the vicinity of the cylindrical member 61, for example, below the adhesive 14. Keeping this state, the user affixes the applicator 10 to a site of application of an active component. The user then pulls the auxiliary liner 60. Through this operation, the patch is guided to the space between the skin and the bottom surface of the body 11 and is folded by the cylindrical member 61 such that the adhesive layer (the active surface of the patch) faces the outside of the arc to stick to the skin.

Figure 17:
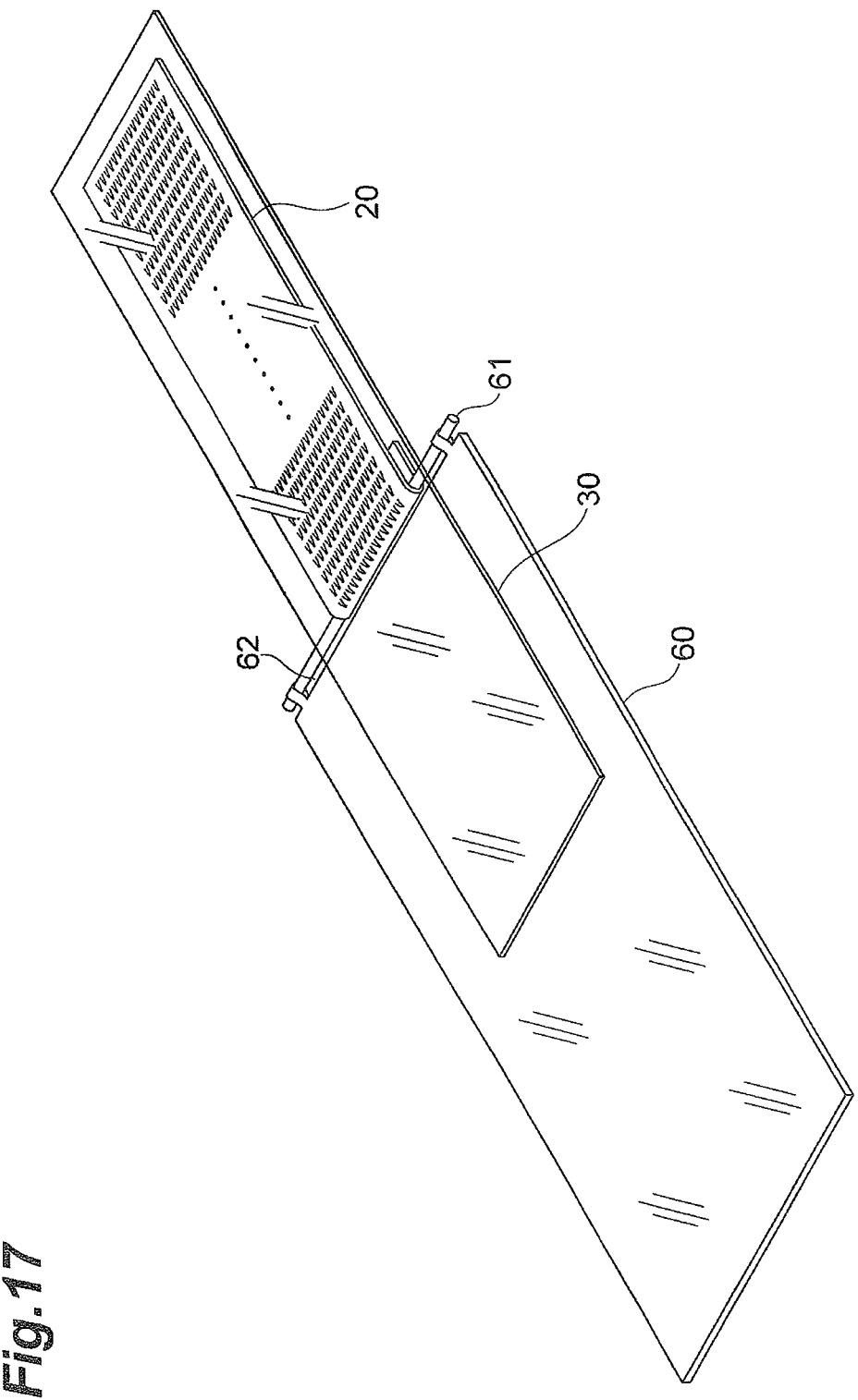
FIG. 17 is a perspective view of a microneedle sheet according to a modification.

The microneedle sheet 20 shown in FIG. 17 can also be used together with the applicator 50. Also in this case, the user can pull the auxiliary liner 60 to apply the microneedle sheet 20 to the skin.

The auxiliary liner 60 shown in FIG. 17 can also applied to the applicator 40 in the second embodiment. An applicator 40A according to this modification is illustrated in FIG. 19. In the applicator 40A, the auxiliary liner 60 is attached to one end side of the liner 42 (the side not connected with the body 41). In this case, the surface of the auxiliary liner 60 and the surface of the liner 42 may be fixed to each other with tape, adhesive, or other means, or these surfaces may not be fixed to each other. The method of attaching the microneedle sheet 20 to the auxiliary liner 60 is the same as in the modification shown in FIG. 17.

When using the applicator 40A, the user passes the auxiliary liner 60 through the first through hole 43 from above to below and further passes its one end through the second through hole 44 from below to above. With this preparation, the auxiliary liner 60 is positioned on the bottom surface side of the applicator 40A between the two through holes 43 and 44, and part of the liner 42 is also positioned on the bottom surface side. In this case, the user puts one end of the microneedle sheet 20 folded in the vicinity of the cylindrical member 61, for example, below the adhesive 45. Keeping this state, the user affixes the applicator 40A to a site of application of an active component. Through a series of these operations, the applicator 40A is fixed on the skin S.

The user then pulls the auxiliary liner 60. This operation allows the cylindrical member 61 to move toward the second through hole 44. The movement of the cylindrical member 61 allows the liner 42 and the microneedle sheet 20 to pass through the first through hole 43 and enter the space between the skin S and the bottom surface of the body 41. The microneedle sheet 20 is bent by 180 degrees in this space by the cylindrical member 61. The microneedles 22 located at the bent portion are then raised from the main surface 21, and the raised microneedles 22 stick into the skin S. The liner 42 pulled apart from the microneedle sheet 20 is guided to the outside of the space through second through hole 44. The user keeps pulling the auxiliary liner 60 to apply the entire microneedle sheet 20 to the skin.

The applicator 40A can also be used to apply any sheet member, as a matter of course. The operation for applying a patch is as follows. First, the user affixes a patch to the liner 42 with the adhesive layer exposed. Alternatively, the patch may be affixed to the liner 42 in advance. In this case, the liner 42 serves the function of a release sheet for the patch. The user then passes the auxiliary liner 60 through the two through holes 43 and 44 in the same manner as described above. The user then puts one end of the patch folded in the vicinity of the cylindrical member 61, for example, below the adhesive 45. Keeping this state, the user affixes the applicator 40A to a site of application of an active component. The user then pulls the auxiliary liner 60. Through this operation, the patch is guided to the space between the skin and the bottom surface of the body 41 and folded by the cylindrical member 61 such that the adhesive layer (the active surface of the patch) faces the outside of the arc to stick to the skin.

As described above, the auxiliary liner having the cylindrical member is applied to the sheet member, so that the sheet member can be folded in the space between the skin and the body of the applicator more easily and more reliably.

The applicator according to the present invention may be either hard or soft. In the case of the applicator partially bent during use, like the applicators 40, 40A described above, at least part (for example, the liner) of the applicator has flexibility to such a degree as to be bent.

REFERENCE SIGNS LIST

10 . . . applicator, 11 . . . body, 12 . . . first through hole (first guide), 13 . . . second through hole (second guide), 14 . . . adhesive, 20 . . . microneedle sheet (sheet member), 21 . . . main surface, 22 . . . microneedle, 30 . . . liner, 40 . . . applicator, 40A . . . applicator, 41 . . . body, 42 . . . liner, 43 . . . first through hole (first guide), 44 . . . second through hole (second guide), 45 . . . adhesive, 50 . . . applicator, 51 . . . body, 52 . . . adhesive, 60 . . . auxiliary liner, 61 . . . cylindrical member.

The invention claimed is:

1. An applicator for applying a microneedle sheet to skin, comprising:
   a sheet-like body having a bottom surface facing the skin, a top surface, a longitudinal direction and an orthogonal, width-wise direction;
   a slit-shaped first through hole positioned in the orthogonal direction of the sheet-like body;
   a slit-shaped second through hole positioned in the orthogonal direction opposite the first through hole; and
   a rectangular adhesive layer provided on the bottom surface of the sheet-like body and surrounding the first and second through holes,
   wherein the microneedle sheet comprises a plurality of microneedles extending along a main surface of the microneedle sheet and the main surface of the microneedle sheet is covered with a liner, wherein when the liner with the microneedle sheet is inserted in the applicator through the first through hole, the microneedle sheet is bent 180 degrees and fixed to the adhesive layer of the applicator adjacent thereto, and the applicator and microneedle sheet and liner are affixed to the skin and the liner is moved in the longitudinal direction of the applicator so the microneedle sheet separates from the liner thereby raising at least one microneedle from the main surface of the microneedle sheet, the at least one raised microneedle sticks into the skin, and the second through hole guides the liner away from the skin.

2. The applicator according to claim 1, wherein one end of the liner is connected with one end of the sheet-like body of the applicator.

3. The applicator according to claim 1, wherein an auxiliary liner including a cylindrical member is attached to the liner, the microneedle sheet is attached to the auxiliary liner such that one end of the microneedle sheet surrounds the cylindrical member, and the microneedle sheet is folded by the cylindrical member in the space.

4. The applicator according to claim 1, wherein at least part of the bottom surface is elevated.

* * * * *